(12) United States Patent
Shoukry (10) Patent No.: US 7,740,603 B2
(45) Date of Patent: Jun. 22, 2010

(54) REMOVABLE FLEXIBLE ORTHOSIS FOR MIDDLE FOOT DAMAGE

(76) Inventor: Kamel Shoukry, Tour Beryl - 20ème Étage, Appt 1, 40, avenue d'Ltalie, Paris (FR) 75013

( * ) Notice: Subject to any disclaimer, the term of this patent is extended or adjusted under 35 U.S.C. 154(b) by 34 days.

(21) Appl. No.: 11/816,523

(22) PCT Filed: Feb. 9, 2006

(86) PCT No.: PCT/FR2006/000299

§ 371 (c)(1),
(2), (4) Date: Dec. 5, 2007

(87) PCT Pub. No.: WO2006/085001

PCT Pub. Date: Aug. 17, 2006

(65) Prior Publication Data

US 2008/0269655 A1    Oct. 30, 2008

(30) Foreign Application Priority Data

Feb. 9, 2005    (FR)    ................................. 05 01315

(51) Int. Cl.
*A61F 5/00* (2006.01)
*A61F 5/37* (2006.01)
*A61F 13/06* (2006.01)
*A41B 11/00* (2006.01)

(52) U.S. Cl. .......................... 602/28; 602/29; 128/882; 128/892; 2/239; 2/242

(58) Field of Classification Search .................. 602/26, 602/27, 28, 29, 5, 22, 60, 61, 62, 66; 128/878, 128/879, 881, 882, 889, 892, 894; 2/239, 2/240, 241, 242, 917, 919; 36/145, 68, 69
See application file for complete search history.

(56) References Cited

U.S. PATENT DOCUMENTS

| 2,708,930 | A | * | 5/1955 | Lowman | ....................... 602/27 |
| 4,271,605 | A | * | 6/1981 | Raczka | ........................... 36/28 |
| 4,313,433 | A | * | 2/1982 | Cramer et al. | |
| 4,597,395 | A | * | 7/1986 | Barlow et al. | .................. 602/27 |
| 5,330,419 | A | * | 7/1994 | Toronto et al. | |
| 5,620,413 | A | * | 4/1997 | Olson et al. | |

(Continued)

FOREIGN PATENT DOCUMENTS

FR    2 606 630    *    5/1988

(Continued)

*Primary Examiner*—Michael Brown
*Assistant Examiner*—Ophelia Hawthorne
(74) *Attorney, Agent, or Firm*—Young & Thompson (57) ABSTRACT

A removable flexible orthosis for the middle foot comprising a) a first metatarsophalangeal collar that encircles and is fixed on the forefoot, and extends transversely from the heads of the first to the fifth metatarsi, and longitudinally from the toe's root towards the mid-diaphysis of the metatarsi, and b) a traction strap comprising at least one end fixed or fixable on the first metatarsophalangeal collar and on the portion of the orthosis designed to be applied on the rear of the foot is provided. The two ends of the stirrup-shaped traction strap can be fixed on the postero-external and postero-internal edges of the first metatarsophalangeal collar on the sides of the foot.

5 Claims, 13 Drawing Sheets

U.S. PATENT DOCUMENTS 5,755,679 A * 5/1998 Selner et al.
6,126,627 A * 10/2000 Brennan .................... 602/65
6,440,159 B1 * 8/2002 Edwards et al. ............ 607/108
6,699,209 B2 * 3/2004 Turtzo ........................ 602/27

FOREIGN PATENT DOCUMENTS

WO    WO 2004/017874    *   3/2004

* cited by examiner

FIG.1Ciii

FIG.1Ciiii

REMOVABLE FLEXIBLE ORTHOSIS FOR MIDDLE FOOT DAMAGE

FIELD OF THE INVENTION

This present invention relates in general to the area of orthoses. More particularly, the invention relates to a removable flexible orthosis for osseous or muscular ligamentary injuries to the midfoot. Concerning in particular a sprain of the midfoot at the Chopart and/or Lisfranc joint, this orthosis aims to relieve the pain, and reduce the oedema, and to allow immediate resumption of walking and healing of the ligamentary injury by drawing together the ligaments of the midfoot.

BACKGROUND

Ankle sprains occur in France at the rate of 6000 cases per day. Of these, 20 to 25% are sprains of the midfoot, which most often go unnoticed since this pathology is little known or not at all, and no specific treatment exists for the moment.

Among the current treatments proposed in the case where there is a diagnosis of sprain of the midfoot, one can mention the Barouk shoe, or the strapping bandage in the form of metatarsal collars, or indeed the plaster boot, all of which support the joint of the midfoot, but without holding it firmly between the forefoot and the rearfoot. Because of this, the resumption of walking is delayed. Elimination of the pain can be achieved only with the plaster boot, and walking can be achieved without aid. In addition, the use of the plaster boot necessitates a treatment to prevent platelet aggregation up to the return to full walking, and can induce secondary trophic difficulties.

The application of elastic bandages (strapping or taping according to the elasticity of the straps) calls for a suitable technique and therefore appropriate training, in order to avoid a garotting effect accompanied by oedema and painful compression points that appear with the sprain. The* other drawbacks of elastic bandages, and especially strapping, are a possible cutaneous intolerance, the obligation to change the bandage or strapping about every three days, and above all the fact that this change has to be effected by specialist staff.

Sprains of the midfoot are one of the most frequent occurrences, and at present there is no orthosis suitable for its treatment. The midfoot is a transition zone between the forefoot or ball, which has a horizontal structure, and the rearfoot, which has a vertical structure. The midfoot has a frontal and unstable structure, since it is multi-articular, and is supported by a multiplicity of ligaments that are subjected to regular stresses (at every step) of some consequence (the full weight of the body).

There are several reasons that render particularly difficult the implementation of an orthosis for the midfoot that is effective and easy to use:
- the anatomic constitution of the midfoot, which includes the innominate joint, the Chopart mediotarsal joint and the Lisfranc tarsometatarsal joint;
- the clinical approach access to the midfoot, rendered difficult by its particular architecture, its mechanical complexity, and the magnitude and impact of the stresses on it.

SUMMARY OF THE INVENTION

The purpose of this present invention is to propose an orthosis for a osseous or muscular ligamentary injury to the midfoot, in particular for a sprain due to stretching, to a partial or total tear of the ligaments in the Chopart and/or Lisfranc joints, including the calcaneocuboid ligaments and the bifurcate ligament. This new orthosis can be managed easily by the patient, and leads to no undesirable effects for the wearer. To this end, the subject of the invention is a removable flexible orthosis that has one part intended to be applied to the rear of the foot and that includes:
- a first metatarsophalangeal collar that is designed to be fitted to the forefoot, extending transversally from the heads of the first and fifth metatarsals, and longitudinally from the rear of the toe roots to the mid-diaphysis of the metatarsal and
- at least one traction strap, at least one end of which is fixed or fixable on the first metatarsophalangeal collar, with the said strap extending between the first collar and the part of the orthosis intended to be applied to the rear of the foot.

SUMMARY OF THE INVENTION

In a manner that is characteristic, the orthosis of the invention draws together the forefoot and the rearfoot, thus gripping the midfoot between them in a vice-like fashion, which holds the damaged elements in a shortened and orientated position. This vice-like action favours the ligamentary and/or osseous healing process, and allows the foot to effectively withstand the external forces, thus considerably limiting the risk of recurrence and returns stability to the foot.

In a preferred implementation variant, the orthosis of the invention also includes a second malleolar collar, of variable height, designed to be placed around the ankle at the level of the inner and outer malleoli. This second collar is preferably, at least in part, fixed to the traction strap, at the top rear edge of the latter.

Other elements can be added to the orthosis of the invention, in order to perform containment of the foot in an orientated manner, such as, for example:
- a metatarso-fibular elastic return strap extending between the first metatarsophalangeal collar and the second malleolar collar, and
- a collar of the tarsus, intended to cover the inner, lower and outer faces of the midfoot, the metatarso-fibular return strap and to close onto itself by partially applying itself onto the second malleolar collar and onto itself by a self-gripping action.

This collar of the tarsus can be fixed to the return strap or on the upper and inner edge of the traction strap thereby covering the midfoot and the return strap so as to hold the latter against the midfoot.

Other characteristics and advantages of the orthosis of this present invention will appear on reading the detailed description that follows of examples of implementation that are provided with reference to the appended, non-limiting drawings of the invention, in which:

BRIEF DESCRIPTION OF THE DRAWINGS

the haematoma of the ankle sprain (i) located on and around the outer malleolus, that of the Chopart sprain (ii) located in front of the premalleolar depression on the midfoot, the double Chopart and ankle sprain (iii), and the Lisfranc sprain (iiii) where the haematoma covers the front of the midfoot and the metatarsal.

DETAILED DESCRIPTION OF THE INVENTION

Figure 1:
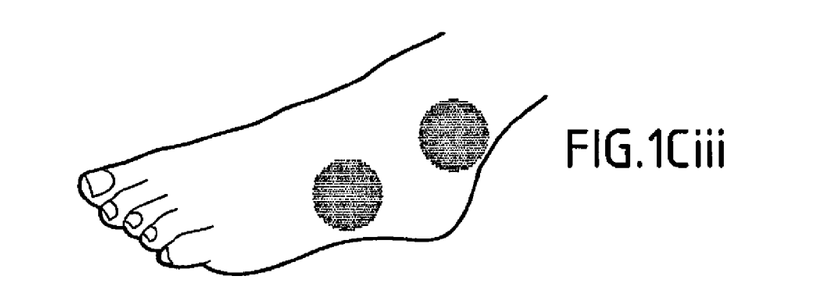
FIG. 1A schematically represents a foot form a three-quarter viewpoint, showing the forces (F1 and F2) exerted on the midfoot when wearing the orthosis of the invention. It can be seen that the foot at rest forms an obtuse angle with the leg (fibular axis and plantar axis)
FIG. 1B shows the position of force F3, which holds the foot at a right angle in relation to the leg.
FIG. 1C shows the position of the haematoma on the outer face of the ankle and of the foot, indicating the presence of ligamentary or osseous lesions at one or more joints.
FIG. 1D shows a foot seen from above and the front, showing broken line AB which represents the size of the foot measured in centimetres, and the circumference (C) of the head of the metatarsal at its widest point.
Figure 1A:
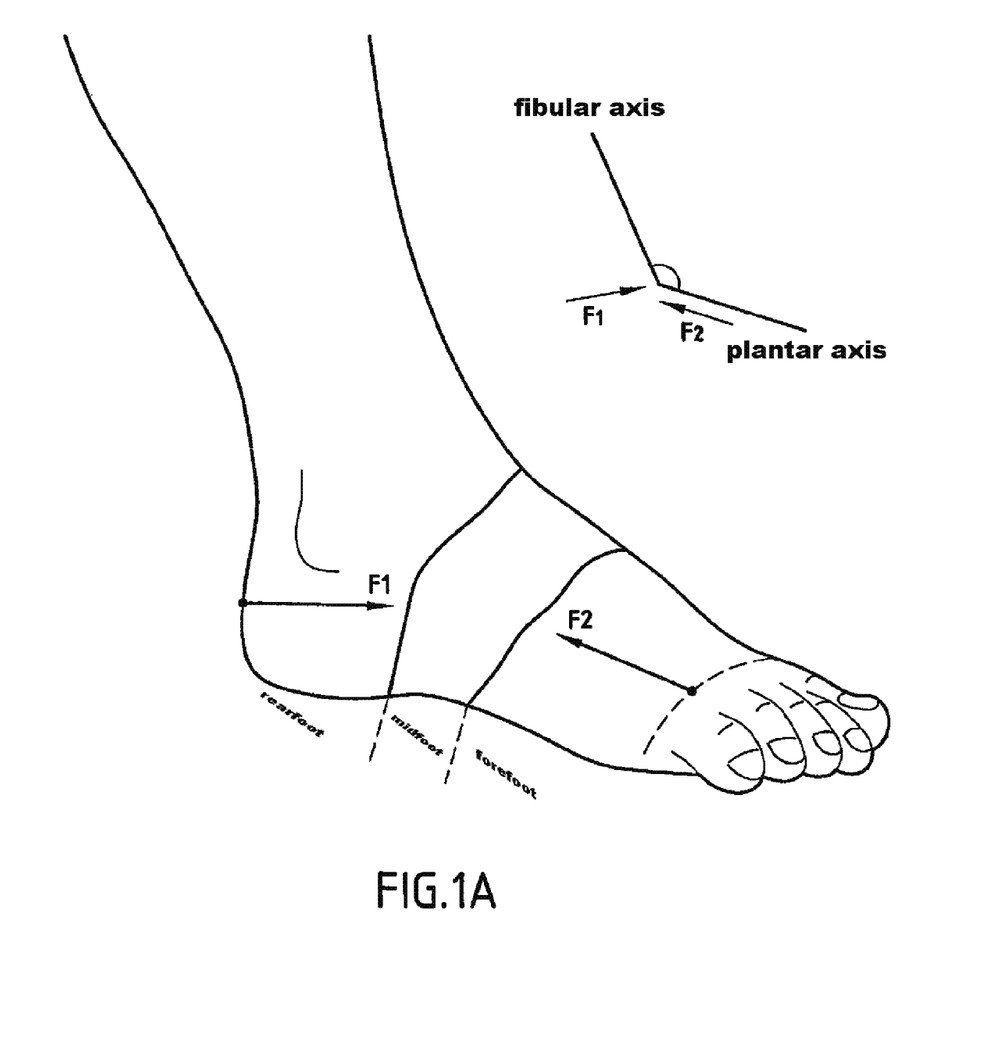

The main function of the orthosis of the invention is the drawing together of the forefoot and the rearfoot in order to grip the midfoot firmly, as shown in FIG. 1 attached, under the effect of forces F2 and F1. This action is used to hold the damaged elements in a shortened and orientated position. The* damaged elements are located under the haematomae, which indirectly indicate the location of the lesion (FIG. 1C). Force F3 directs the sole of the foot (the plantar axis orients the sole in relation to the axis of the leg—the fibular axis). It shortens the path of the peroneal muscles, which has the effect of causing the contracture or spasm, and therefore the pain, to disappear. This orientated containment according to the reconstitution of the anatomy concerns the Chopart and of Lisfranc joints respectively. It is achieved by means of a set of straps and collars that are assembled together and judiciously oriented to generate the different lines of force.

Figure 1D:
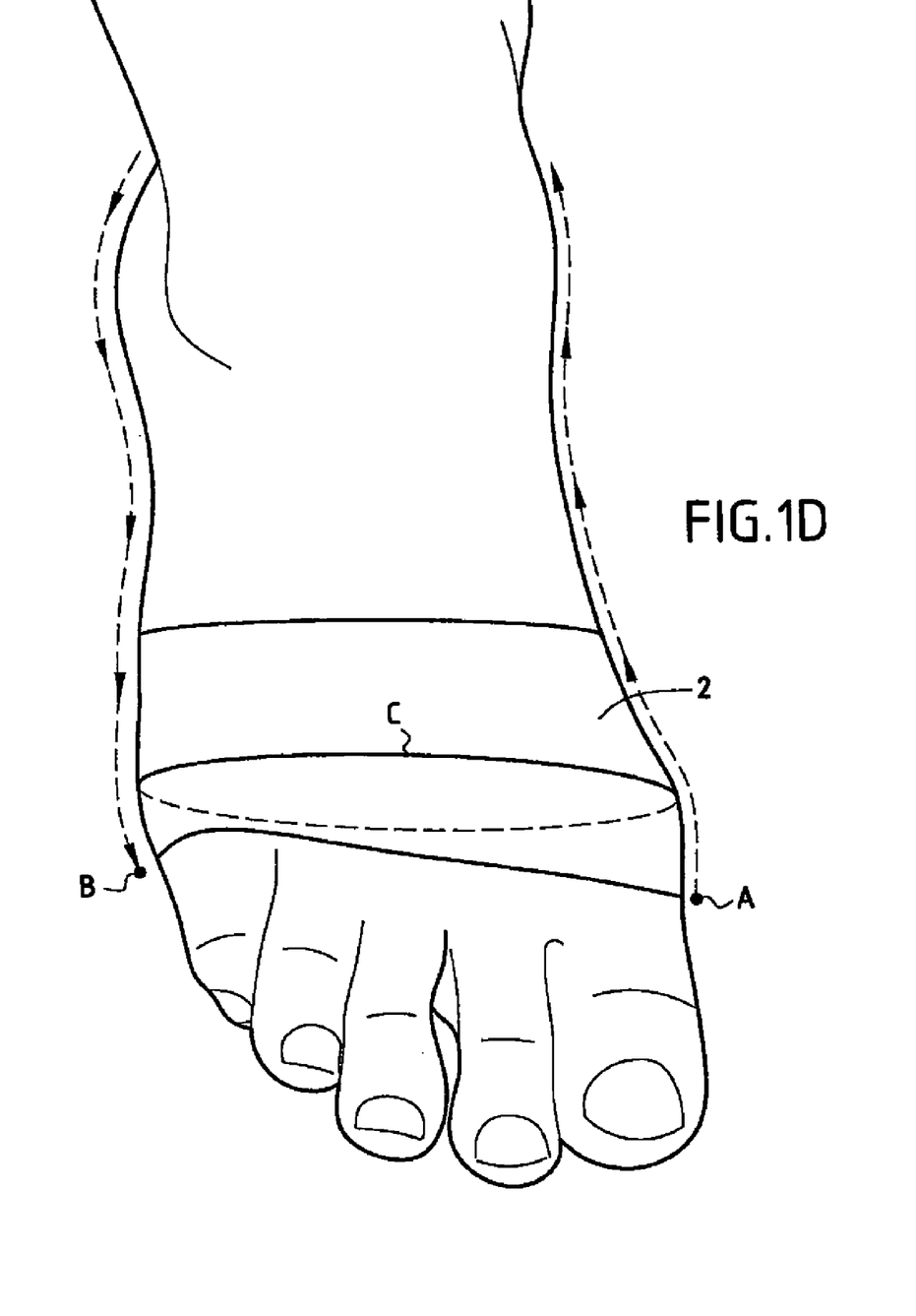
Figure 2A:
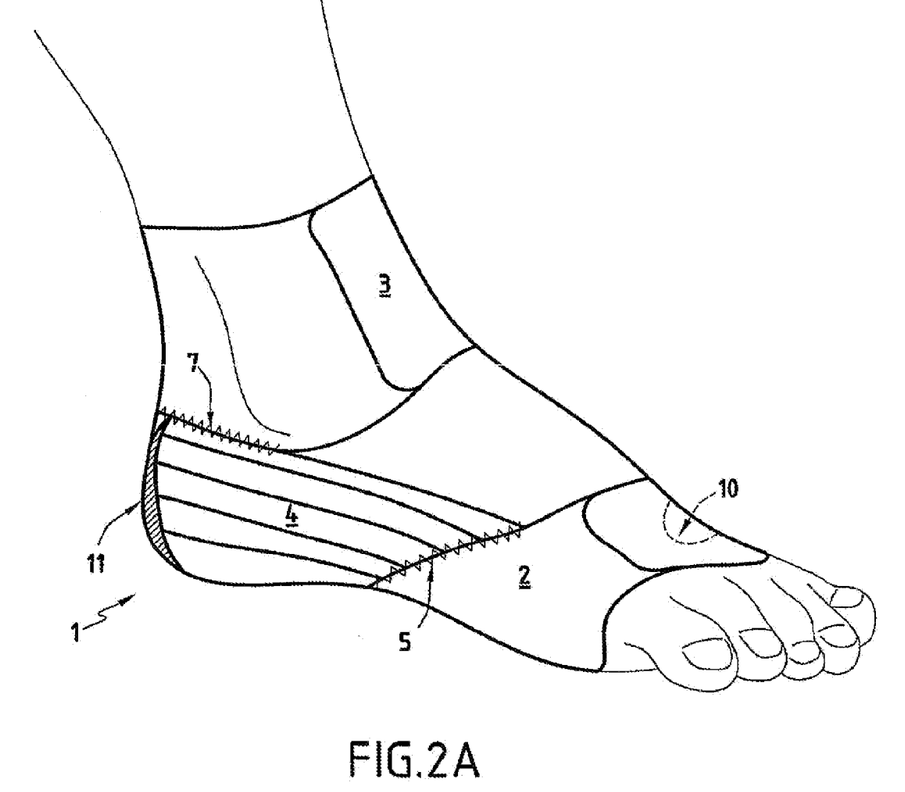
FIGS. 2A and 2B represent a first implementation example of the orthosis of the invention, which includes the first metatarsophalangeal collar, the traction strap, and the second malleolar collar, positioned on a foot, seen in outer profile in FIG. 2A and seen in inner profile in FIG. 2B.
Figure 2B:
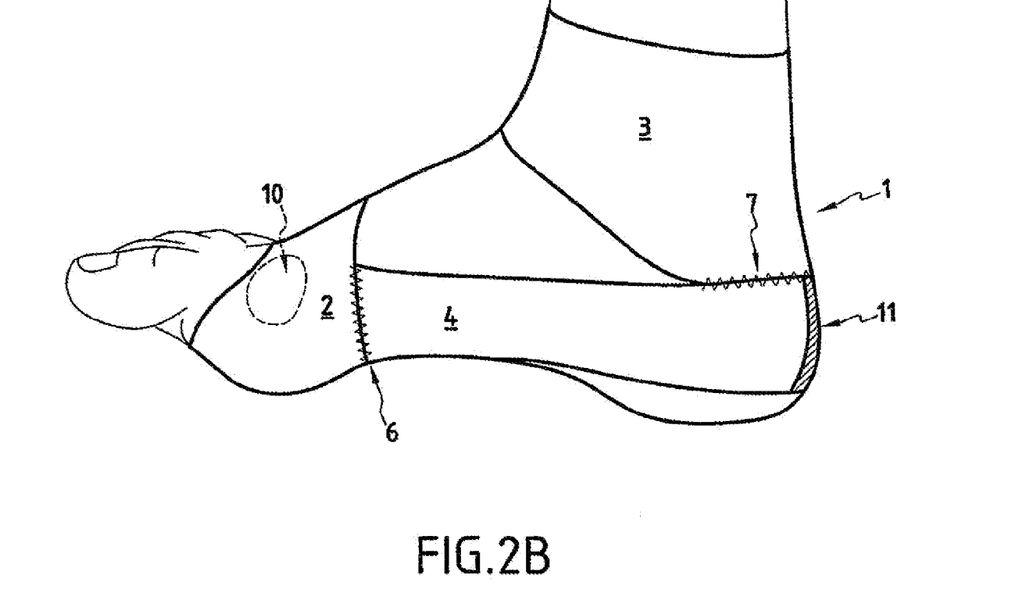

According to the first implementation example, illustrated in FIGS. 2A and 2B, the orthosis 1 is specially designed for the treatment of ligamentary injuries ri the outer midfoot. It includes an adjustable, annular first metatarsophalangeal collar 2, acting as a front anchor, and a traction metatarso-calcaneo-metatarsal strap 4 in the form of a stirrup, with the combination of this first collar and this traction strap used to exert the traction effect necessary for firmly gripping the midfoot between the rearfoot and the forefoot. The first metatarsophalangeal collar 2 covers the forefoot, extending transversally between the foot of the heads of the first and fifth metatarsals and longitudinally from the rear of the base of the toes to the mid-diaphysis of the metatarsal. This first collar 2 has a width (the dimension measured in the longitudinal direction of the forefoot) that can be between 5 and 10 centimetres, according to the size of the individual. It covers and grips at least the circumferential zone C (FIG. 1D) between the prominent heads of the first and fifth metatarsals, which is the broadest area of the foot, and the zone that is in front of this circumferential zone C, in the direction of the toes. Thus the first metatarsophalangeal collar 2 is perfectly locked in position during application of force F1 exerted by the traction strap 4. In FIG. 1D, this first collar 2 extends from the toe roots to mid-length of the metatarsal diaphyses.

In the first example, the traction strap 4 has the form of a stirrup, incorporating the part of the orthosis that is intended to be applied to the rear of the foot and forming an inner traction strap and an outer traction strap on either side of this rear part. However, the invention is not limited to this methods of implementation, since the rear part can be independent of the traction strap, with the latter capable of being inner or outer only. The rear part of the orthosis, which in the first example is the elbowed part of the traction strap 4, is applied to the zone of the calcaneum that constitutes, with circumferential zone C above, the second anchoring zone of the orthosis, allowing application of forces F1 and F2 and exerting a firm grip of the midfoot between the forefoot and the rearfoot. It is for this reason that the traction strap 4 can be described as metatarso-calcaneo-metatarsal.

It is preferable to avoid the application of the rear part of the orthosis to the Achilles tendon area, which would be liable to constitute an annoyance, or even a localised trauma, due to the forces involved.

The* two ends of the traction strap 4, in the form of a stirrup, are attached to the first collar 2 by two lines of stitching 5 and 6 effected symmetrically along the inner and outer rear edges of the said first collar 2.

In a preferred manner, the orthosis 1 includes a second adjustable annular malleolar collar 3, acting as an anchor at the ankle.

At its rear part, the traction strap 4 is attached by partial stitching 7 to a limited sector of the lower selvedge of the second malleolar collar 3. Attached on either side of the traction strap 4, there can be one or more tapes 28, located on the plantar face of the foot (visible in FIG. 3b). This tape 28 is used to prevent the extrusion of the foot from the orthosis downwards, because of poor fitting of the orthosis.

Naturally there can be several lengths of traction strap 4 according to the size families chosen. The circumferential adjustment of the first metatarso-phalageal collar 2 is preferably achieved by a self-attachment technique. As indicated previously, the circumferential metatarsal zone C (FIG. 1D, line C) plays an essential part in anchoring the orthosis to the forefoot. It is therefore this measurement that is taken into account when choosing the size of the orthosis, complemented by the size of the foot. The circumference C is measured by taking as a reference the most widely separated points between the head of the metatarsal at the first metatarsal and the head of the fifth metatarsal. Note also that the length (in centimetres) measured from the root A of the first toe passing via the inner face of the foot, via the rear of the heel and then returning to the outer face of the foot up to the root B of the fifth toe. This measurement AB will be used to determine the size of the fitting desired for the orthosis.

Advantageously, the orthosis of the invention, in all of its variants, can be created in sizes that range from paediatric size up to adult sizes, in left and right pairs.

In this first implementation example, the metatarsophalangeal collar 2 comes in the form of a tape whose end portions are equipped with attachment elements of the hook & loop (Velcro) self-attachment type allowing the said tape to be closed onto itself at a length that is adjustable, thus enabling the dimension of the collar to be adjusted to suit the actual circumferential zone C of the user.

FIGS. 3A to 3D illustrate a second implementation example of an orthosis 1' that also includes an elastic metatarso-fibular return strap 8 and a third collar on the tarsus 9, attached to each other at 90° by a line of stitching at a distance such that the third collar on the tarsus 9 surrounds only the midfoot of the patient. In the implementation example of FIG. 4, the collar of the tarsus 90 is sewn on the top inside edge of the torsion strap 40.

Figure 1B:
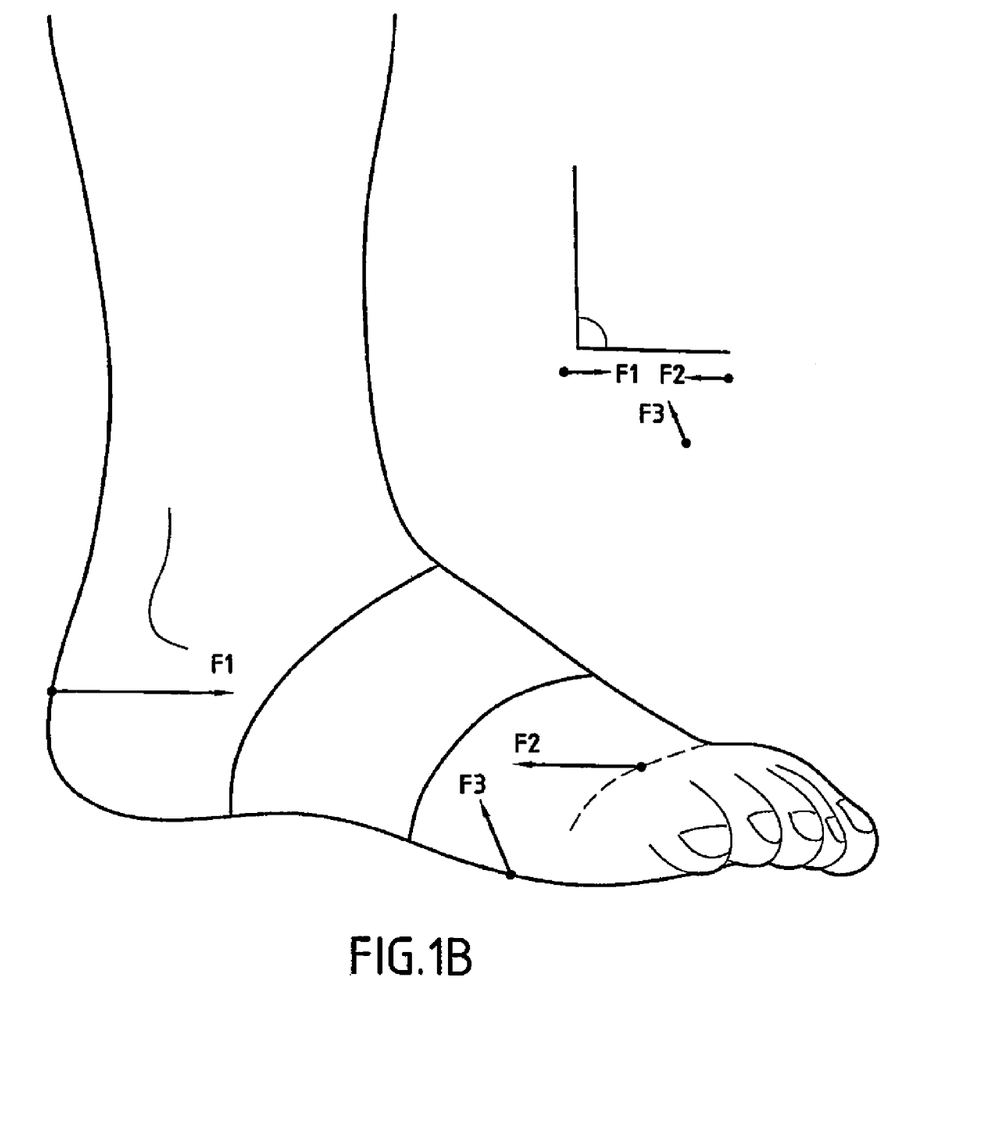
Figure 3A:
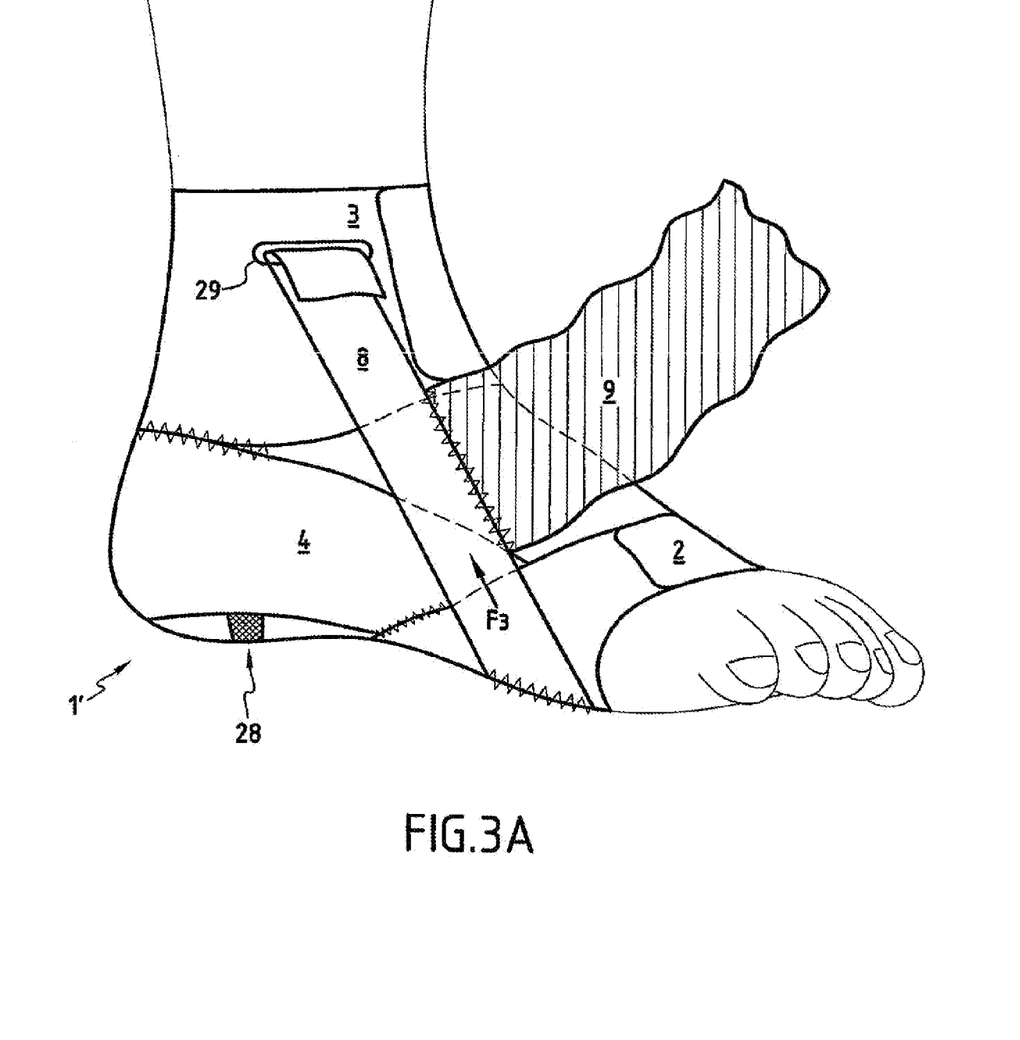
FIGS. 3A to 3D illustrated the orthosis of the invention according to a second implementation example, which also includes a return strap and a third collar of the tarsus on a foot, seen in outer profile in FIG. 3A, seen from the lower face in FIG. 3B, seen in outer profile with the third collar of the tarsus folded over in FIG. 3C and seen in inner profile in FIG. 3D.
Figure 3B:
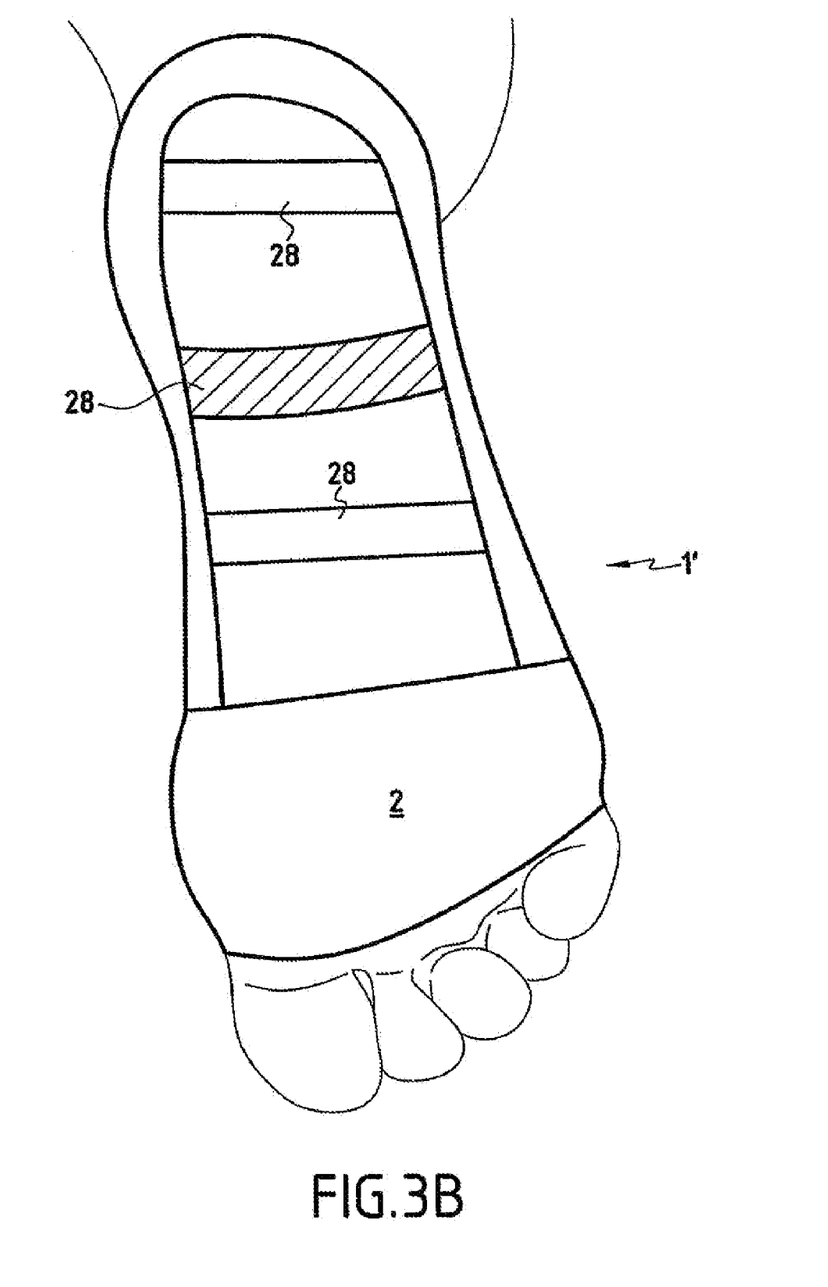
Figure 3C:
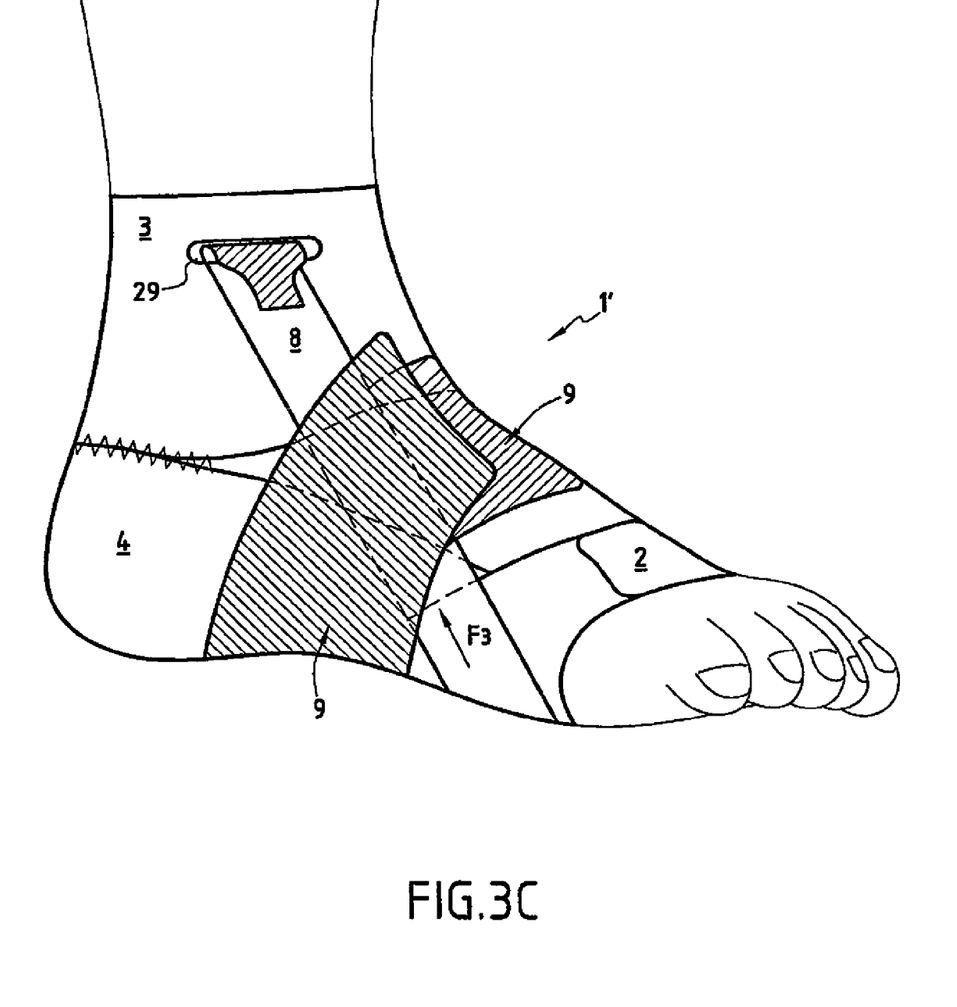
Figure 3D:
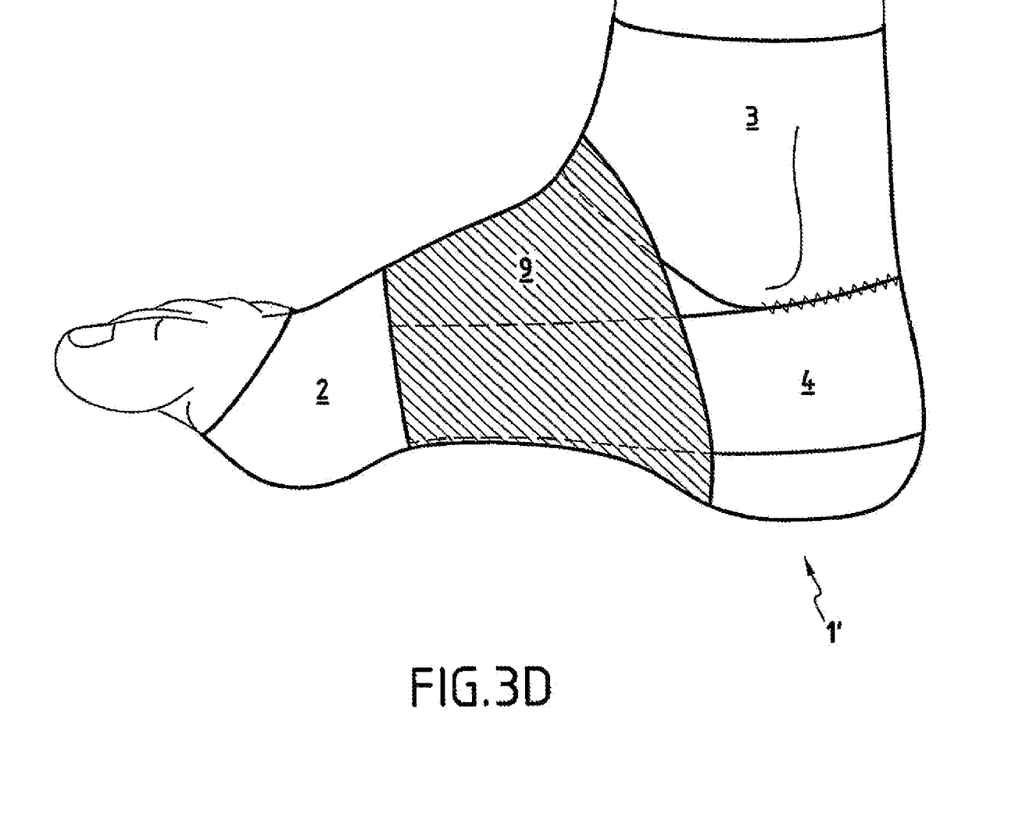
Figure 4:
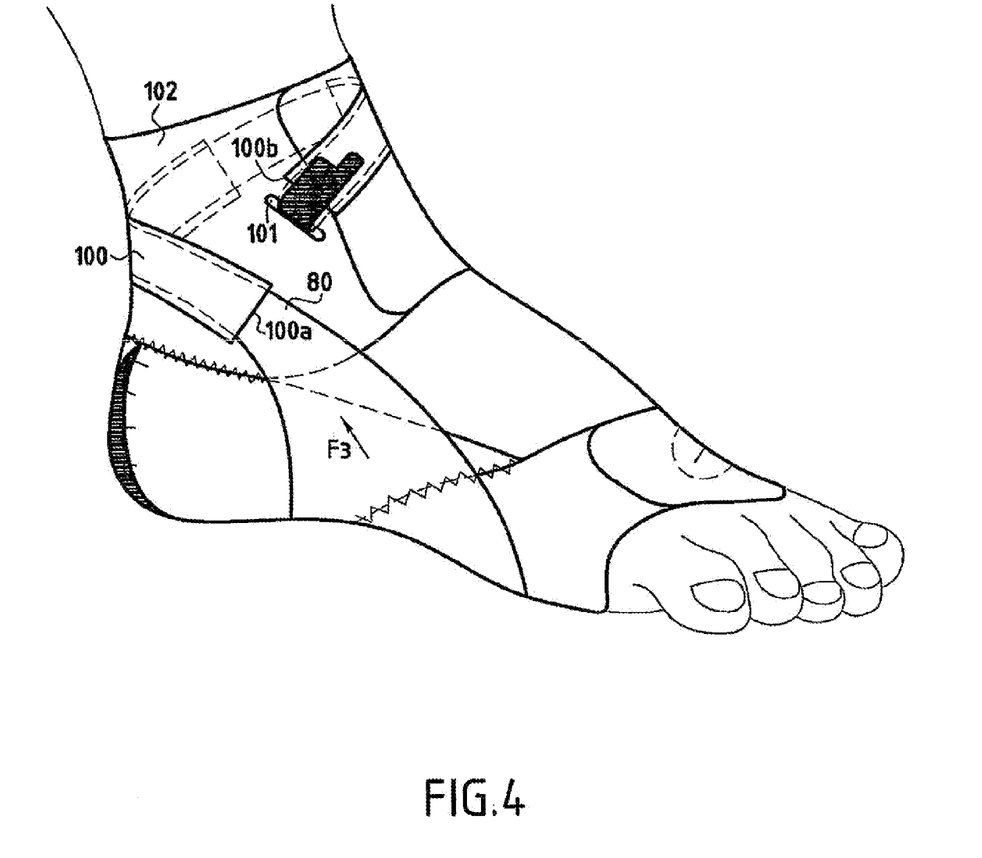
FIG. 4 illustrates another variant of the orthosis of FIG. 3, seen from the outer profile of the foot, with a trapezoidal return strap, the lower end of which is fixed onto the metatarsophalangeal collar and on the traction strap, and the top end of which goes all around the rear of the ankle, being held in a loop so as to anchor itself in front of the malleolar collar.

The function of the return strap 8 is to hold the outer edge of the foot at a right angle and to incline the foot in relation to the leg (the valgus position, FIG. 1B, force F3). It is attached by one of its* ends to the first metatarsophalangeal collar 2 by a line of stitching 30, and bears upon the outer edge of the said first metatarsophalangeal collar 2. Its other end is hooked by a self-attachment arrangement to the fibular incline of the malleolar collar 3, or passes through a loop (29 in FIG. 3A) and turns back onto itself to be anchored by a self-attachment arrangement. In the implementation example of FIG. 4, the return strap 80 passes through a loop 100 that loops around via the rear of the Achilles tendon and is then attached by means of a loop 101 in front of the malleolar collar 102. This loop 100 is sewn to the rear face of the malleolar collar (102 in FIG. 4) and angled so that its outer end 100a is located at the outer malleolus and its inner end 100b is located at the top edge of the malleolar collar 102. The action of the return strap 8 is illustrated in FIGS. 3A and 4. Force F3 lifts the outer part of the foot and then entire forefoot, according to the tension that is exerted during the fitting. The plantar axis of the foot is at a right angle in relation to the fibular axis of the leg.

In order to allow this return strap 8 to perfectly hug the anatomy of the trajectory that it follows on the foot and the outer edge of the ankle, it is held down by the third collar of the tarsus 9, which comes in the form of a tape that envelops the midfoot and comes back onto itself beyond the line of stitching 31 in and secured by self-attachment elements.

In the implementation example illustrated in FIG. 3A, the third collar of the tarsus 9 is secured by stitching to the return strap 8. This third collar 9 could also be fitted to the top rear inner edge of the traction strap 4 (not visible in FIG. 3A). Likewise the return strap 8 could have a trapezoidal configuration, whose large base would be fixed by a line of stitching 30 extending over the whole length (considered in the longitudinal direction of the foot) of the first metatarsophalangeal collar 2 and over a part of the length of the traction strap 4.

Finally the second malleolar collar 3 could rise along the full height of the ankle and even further, possibly being divided down into several sections of strap, anchored to them by self-attachment. In this case, the upper section of tape preferably has inside it a non-slip material to improve the retention in position of this second malleolar collar 2.

Those practised in the art will understand the importance of choosing correct angling of the collars and straps in relation to each other, so that the correctly oriented forces relieve the patient, and in particular favour the healing of the ligaments.

In order that the orthosis 1 or 1' can be worn regularly, it must be effective and comfortable. The comfort is achieved by the choice of the textile materials and padding materials. The* tensions applied to the straps require protection of the skin in certain well-defined zones. This is the case for the traction strap 4 which, as illustrated in FIG. 2, is covered on its inner face, at the heel, by an insulating material 11, such as a thin layer of neoprene or silicone for example, attached locally onto the strap 4. By virtue of its heel-pad shape at the calcaneum, the orthosis 1 avoids creating tendonitis of the Achilles tendon. A lining pad 10 of suitable shape can be applied to the inner part of the first metatarsophalangeal collar 2. This piece, which can be in neoprene or silicone, protects against subjacent soreness of the big toe (FIG. 2).

The inner surface of the first metatarsophalangeal collar 2 is preferably covered with a layer of a non-slip material with a high friction coefficient, such as silicone or neoprene for example, to prevent it from slipping at the midfoot due to force F2 exerted by the traction strap 4, or to prevent it from pivoting due to eccentric force F3 of the return strap 8.

The first collar 2 can, for example, be made from a jersey knitted appliance in polyamide/lycra with high longitudinal elasticity, affixed to a layer of neoprene with a thickness of around 1.5 to 2.5 mm, or can be made completely from neoprene or any other material. During the fitting, under tension, of the first collar 2, the latter deforms, closely hugging the contours of the foot and in particular the protuberance formed locally by the heads of the first and fifth metatarsals. This application under tension, combined with the non-slip effect of the neoprene, achieves the desired anchoring of the orthosis at the forefoot, designed to withstand force F2 of the traction strap and possibly force F3 of the return strap.

The role of each constituent of the orthosis of the invention in the treatment of a sprain of the midfoot is indicated below:

the traction strap 4 (elastic in traction) and the first metatarsophalangeal collar 2 effect a drawing together of the forefoot and the rearfoot, holding the midfoot firmly between them (longitudinal axial support), thus drawing together the bones of the tarsus and the distended or torn ligaments, and having as a consequence the reduction or even the disappearance of the pain, and the drawing together of the distended or torn ends of the ligaments of the outer midfoot (Chopart and Lisfranc joint), and possibly a non-slip element placed on the inner face of the traction strap 4 to stop it from slipping;

the third collar of the tarsus 9 holds the bones of the tarsus in position on the transverse axis;

the elastic return strap 8 prevents the dropping of the forefoot plantar and varus flexion and directs the foot into dorsal and valgus flexion, depending on the extent of recovery felt by the patient, by relieving the contracture of the peroneal muscles;

the containment of the foot contributes an anti-oedematous effect.

The concept described above can also be achieved with an orthosis whose functions are identical, but with a different industrial implementation, taking advantage of the most recent technological developments of the rectilinear knitting machine, with computer control of all its functions.

In this implementation variant, the orthosis of the invention totally envelops the ankle and the foot by means of a knitted structure in the form of a sock. This has the advantage of being able to include two rigid elements in the height direction, so as to stabilise the ankle in the frontal plane and so avoid varus of the foot. It is particularly recommended in the case of a double sprain, when a sprain of the ankle is accompanied by a sprain of the midfoot that could go unnoticed and therefore remain untreated.

Figure 5:
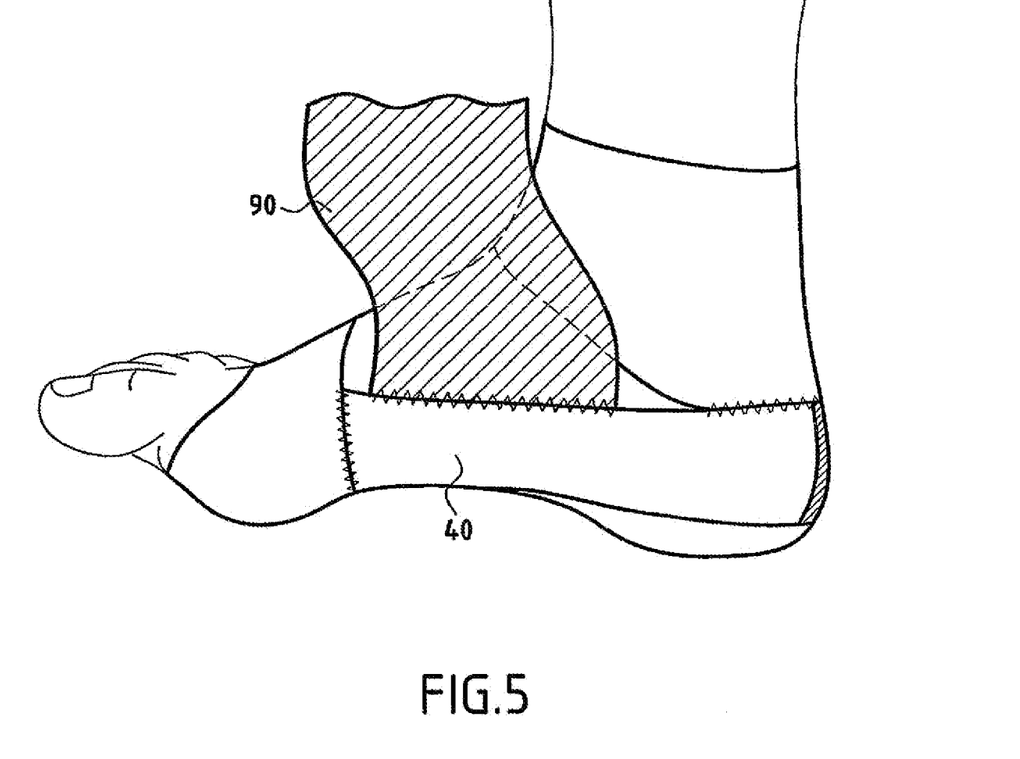
FIG. 5 illustrates an orthosis in which the third malleolar collar is fitted to the inner edge of the traction strap, seen in inner profile of the foot.
Figure 6:
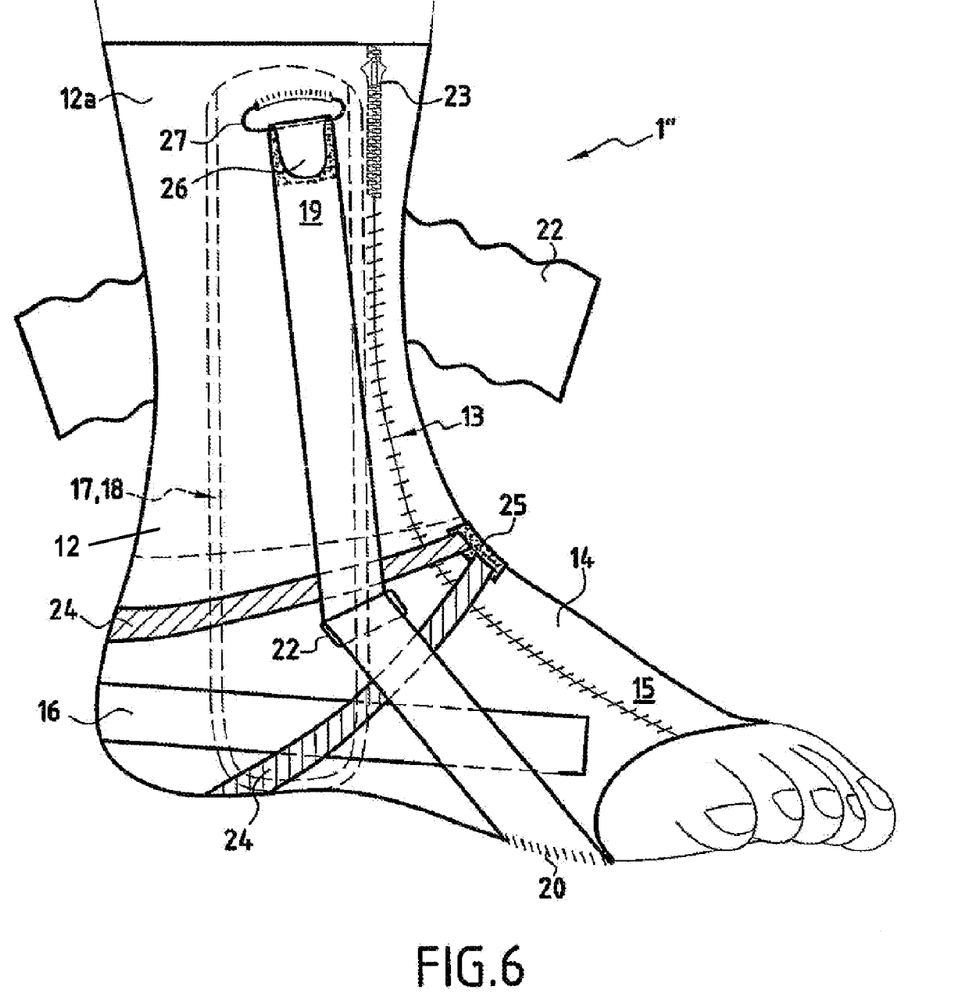
FIG. 6 illustrates an implementation example of the orthosis of the invention, which presents a knitted structure in the form of a sock.

One can well understand the advantage of this variant of the invention in the view of FIG. 5, which illustrates a third implementation example.

The orthosis 1" of the invention is composed of a knitted element 12 that is closed onto it by means of flat stitching 13. The volume of the heel and natural curvature leg and foot are fashioned by the computerised control of the number of stitches to each row of knitting so as to obtain a three-dimensional result.

The containment of the orthosis is achieved by the presence, using a process that is well known, of a elastic thread, knitted or incorporate at each row of knitting, and by the presence of an elastic weft thread every two rows of knitting, except in the area of the tarsus 14 so as to exert a higher pressure and so reduce the oedema.

The orthosis 1" includes a first metatarsophalangeal collar 15 with a material with a high friction coefficient, sewn or otherwise applied to the interior of the knitted appliance at the forefoot. This first collar 15 has the advantage of the anatomic shape of the forefoot (the widest metatarsal circumference).

The containment force of the elastic knitted appliance is necessarily complemented by a traction strap or stirrup as described in the first example above. FIG. 5 shows a traction strap 16 placed on the outer face.

Two long ducts 17 (one located on the outside and the other on the inside of the foot), preferably implemented in astrakhan fabric, are stitched onto the upper part of the orthosis 1" that surrounds the ankle and that forms a second malleolar collar 12a. These allow the insertion, the positioning and the retention of two rigid elements 18 padded by foam for comfort and protection of the skin. The rigid elements extend from the sole of the foot to a height of 12 centimetres or more above the point of the fibular malleolus. Attachment straps 24, preferably two on the inside and two on the outside of the ankle, with as their respective origins the rear zone and the lower zone of the heel, going around the instep at the front to attach itself by Velcro 25. The attachment straps 24 are used to stabilise the bottom ends of the rigid elements 18 below the malleoli or ankle bones.

In cross section, these rigid elements 18, are shaped to hug the anatomic shape of the leg/ankle/malleolus zone, with the outer duct 17 acting as an attachment surface for the top end of the elastic return strap 19. This return strap 19, of very high containment value, is fixed by stitching 20 to the first metatarsophalangeal collar 15, at the correct angle as explained earlier. It lifts the outer part of the foot and then entire forefoot according to the tension that is imparted to the element, in accordance with the improvement rate felt by the patient. This return strap 19 is fitted with a self-attachment system, of the hook and loop (Velcro) type for example, and is anchored by its top end to the outer face of the duct 17, or passes through a loop 27 and returns onto itself, anchored by a self-attachment arrangement 26.

In order to facilitate the fitting of the orthosis 1", the containment sock 12 is equipped at the top end with a zip fastener 23. This substitute for the assembly stitching 13 over a height that ranges from the level of the malleoli to the top end of the sock.

The orthosis can include a loop 21 that is used to attach the return strap 19 to the knitted element 12.

A fixing tape 22, fixed onto the rear of the sock 12, closes onto itself above the malleoli and prevents any movement of the rigid elements or the detachment of the strap 19.

In the methods of implementation described above, the different straps used in the composition of the orthosis of the invention, namely the return straps 8, 19 and the attachment straps 24, are positioned on the outer face of the orthosis 1', 1" respectively. These straps can also be positioned on the inner face of the orthosis 1' or 1", in which case they are lined on the inside with a layer of textile material designed for direct contact with the skin.

The orthosis of the invention has many advantages for patients who present an injury of the midfoot and possibly of the ankle. The wearing of this orthosis, which is easy to fit and remove, favours its use by the patient, provides safety and security in movement, encourages the resumption of walking, and starts the process of re-education. The grip-like action on the midfoot relieves the pain, favours healing, and allows the foot to withstand external forces, considerably limiting the risk of recurrence. Containment of the foot, which is achieved by the various elastic elements that make up the orthosis, favours drainage of the oedema.

The invention claimed is:

1. A removable flexible orthosis for injuries to the midfoot, comprising:
    a first metatarsophalangeal collar designed to be fitted to the forefoot, extending transversally on the heads of the first and fifth metatarsals, and longitudinally from the rear of the toe roots to the mid-diaphysis of the metatarsals,
    at least one traction strap, wherein at least one end of the traction strap is fixed or fixable on the first metatarsophalangeal collar, the traction strap extending between the first metatarsophalangeal collar and the rear of the foot and surrounding the back of the heel bone or calcaneus,
    a second malleolar collar designed to be placed around the ankle, wherein the second malleolar collars is fixed, at least in part, to the traction strap,
    a return strap extending between the first metatarsophalangeal collar and the second malleolar collar, wherein the return strap is fixed to the first metatarsophalangeal collar and to the second malleolar collar along an attachment line that extends from the toe root to the tarsal bones on the outer or inner edge(s) of the foot, and
    a third tarsal collar designed to be placed around the foot to cover the bones of the tarsus and to close onto itself, wherein at least one end of the third tarsal collar is fixed to the return strap.

2. The flexible orthosis according to claim 1, further comprising:
    a knitted element in the form of a sock that is closed onto itself by means of stitching or stitching and a zip fastener, the knitted element comprising a part that acts as the second malleolar collar, and
    an inner duct and an outer duct, fixed onto the part of the knitted element that acts as the second malleolar collar, for the placement of rigid elements, the outer duct capable of acting as an attachment surface for the end of the return strap.

3. The flexible orthosis according to claim 2, further comprising
    attachment straps on the inside and on the outside of the ankle, having as their origin the rear and the bottom of the heel and intended to stabilize the bottom ends of the rigid elements against the malleoli.

4. The flexible orthosis according to claim 3, wherein the return strap and the attachment straps are positioned either on the outer face of the orthosis or on the inner face of the orthosis, or symmetrically on both sides of the orthosis and crossing on the dorsum of the foot.

5. The flexible orthosis according to claim 1, wherein said third tarsal collar is fitted to the top inside edge of the traction strap.

* * * * *